United States Patent

Boinot

[11] Patent Number: 4,680,011
[45] Date of Patent: Jul. 14, 1987

[54] DENTAL CONTRA-ANGLE HANDPIECE WITH MEANS FOR ILLUMINATING THE TREATMENT AREA

[75] Inventor: Jean-Claude Boinot, Roulans, France

[73] Assignee: Micro-Mega S.A., Besancon, France

[21] Appl. No.: 844,356

[22] Filed: Mar. 26, 1986

[30] Foreign Application Priority Data

Mar. 27, 1985 [FR] France ................................ 85 05016

[51] Int. Cl.$^4$ ................................................ A61C 1/00
[52] U.S. Cl. ........................................................ 433/29
[58] Field of Search ................................... 433/29, 126

[56] References Cited

U.S. PATENT DOCUMENTS 4,561,845 12/1985 Meller ..................................... 433/29

Primary Examiner—Robert Peshock
Attorney, Agent, or Firm—Robert E. Burns; Emmanuel J. Lobato

[57] ABSTRACT

A dental handpiece comprises a front part with a head and a handle part. The head is provided with at least one miniature bulb mounted therein for illuminating the treatment area and the dental handpiece is provided with means for supplying electric power to the bulb. At the junction between the front part and the handle part of the handpiece is disposed an axially extending spring blade contact mounted in the handle part. When these parts are operatively connected, the spring blade contact is spaced from a fixed contact carried by the front part. A switch comprised of a push-knob is mounted on the handle part adjacent to the spring blade contact and operative to actuate the spring blade contact for closing the light circuit. The spring blade contact acts as a return spring to the push-knob so as to normally urge it to its open-circuit position. Thus, the dental surgeon can light the bulb only when required.

19 Claims, 3 Drawing Figures

DENTAL CONTRA-ANGLE HANDPIECE WITH MEANS FOR ILLUMINATING THE TREATMENT AREA

BACKGROUND OF THE INVENTION

The present invention relates to a dental contra-angle handpiece with means for illuminating the treatment area, which comprises a front part including the head in which the tool is clamped, this head being provided with at least one miniature bulb, a handle adapted to be detachably connected to said front part, and a rear socket adapted to be fitted to the rear end of said handle and provided with electric contact means adapted to engage matching contact means provided on the rear face of the handle for supplying electric power to said bulb.

It is already known to facilitate the task of dental surgeons by incorporating lighting means adapted to illuminate the treatment area in the handpiece.

In some known device the light source consists of an optical fibre having its output and located beneath the contra-angle head and supplied with light rays from a source consisting of a halogen lamp disposed at the rear end of the contra-angle. However, in such an arrangement a continuous fiber is required for any gap therein which would absorb at least thirty percent of the light intensity and besides the fiber end on the bur side must be safely protected against movement. Furthermore, in this arrangement the contra-angle head must be independent of the fiber support so that, in case of need, this head can be replaced by another head on the handpiece body without changing the optical fiber. Now this may constitute a serious inconvenience, in particular for the assembly of the various component elements of the contra-angle.

Handpieces incorporating one or a plurality of miniature bulbs as a light source are already known, but so far none of the suggested structures provides a simple and reliable electrical connection of the different parts. Since the contra-angle body must be easily detached from the head to permit a quick replacement of the head according to the specific operations contemplated, all the lighting systems proposed heretofore are confronted with the problem of properly interconnecting the various elements. In fact, the conducting leads extending through the contra-angle body must be connected without any difficulty to the conducting leads of the contra-angle head, and the connecting means must be both simple and reliable inasmuch as the handpiece is to be frequently assembled and disassembled in actual service.

SUMMARY OF THE INVENTION

It is a primary object of the present invention to provide a dental handpiece provided with the lighting means comprised of at least one miniature bulb to which electric power is supplied through conducting leads arranged within the various elements such that at the above-mentioned junction problems are safely avoided and the leads can be easily connected or diconnected with respect to the power source.

For this purpose, the handpiece according to the present invention is characterized by claim 1.

With this arrrangement, the various elements can be manufactured and assembled without difficulty and economically, while warranting perfect, reliable electrical connections. Morever, in accordance with the present invention, the bulb contact is established immediately when the dental surgeon grips the contra-angle. Since the push-knob projects radially from the contra-angle peripheral surface, he or she can actuate the switch with the hand holding the contra-angle. On the other hand, when the dental surgeon releases the handpiece, the contact is opened and the bulb is switched off.

In a preferred form of the embodiment, the contacts on the rear surface of the handle are comprised of a pair of concentric annular tracks. These rear annular contacts facilitate the connection with a rear socket of which the electrical contacts provided on its front surface are connected under resilient pressure to the annular tracks in relative annular positions of the socket and the handle of the handpiece. It is thus possible to dispense with positioning means between the portion and the handpiece handle, and these two elements can rotate freely relative to each other. The rear socket may incorporate a driving micromotor and/or batteries for energizing the bulbs.

Preferably, the bulb is inserted into a metal socket adapted to be screwed into the handpiece body and provided with a diametral slot for engagement, with a screwdriver, so that a burn-out bulb can be easily replaced. The bulb and its socket can be disposed close to a tool, for example a bur, and set in a very slightly inclined direction with respect to the tool axis. Such an arrangement is not afforded with optical fibers which cannot be bent to any sharp angle.

BRIEF DESCRIPTION OF THE DRAWINGS

The invention will now be described more in detail with reference to the accompanying drawings illustrating diagrammatically by way of example a typical form of embodiment of the improved handpiece. In the drawings.

DESCRIPTION OF THE PREFERRED EMBODIMENTS

Figure 1A:
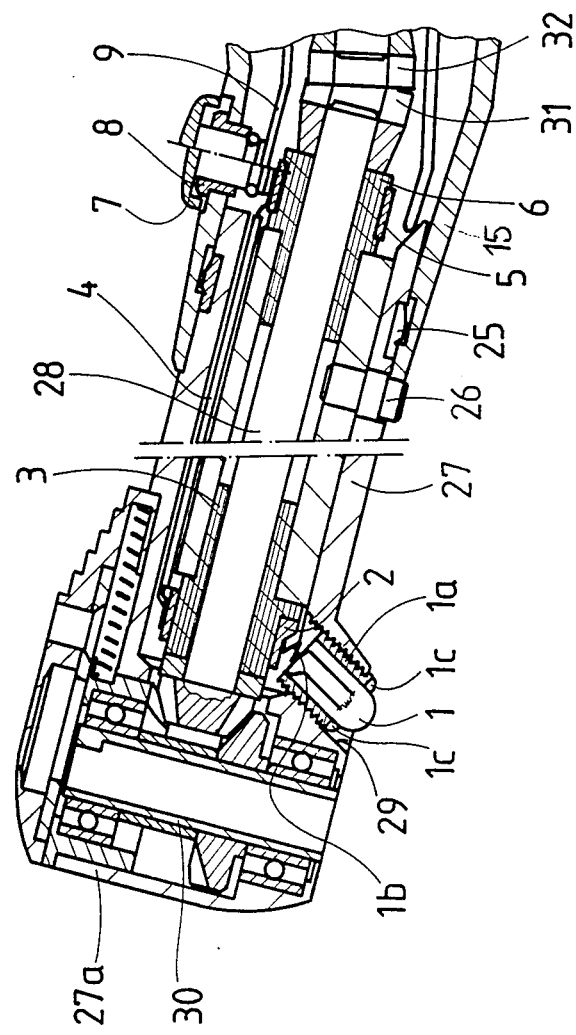
FIG. 1a is a longitudinal section showing the front section of the handpiece with the contra-angle head fitted thereto.

The contra-angle handpiece illustrated in the drawings comprises of a tubular handle 15 and a front part or tubular arm 27 incorporating a head 27a in which a tool (not shown) is detachably fitted in a tool holder 30. This tool holder 30 is driven as conventionally by a first rotary shaft 28 disposed with is the front part 27 and provided at its rear end with a pinion 31 detachably mesh with a corresponding pinion 32 rigid with the front end of another or second rotary shaft 28a rotatably mounted in the handle 15. This second shaft 28a, in the example illustrated, is arranged to be driven by a micromotor (not shown) secured to the rear end of handle 15. In this case, the nose of the micromotor protrudes into the handle and its output shaft is in driving engagement with the fork 33 formed at the rear end of shaft 28a. The front part or tubular arm 27 is detachably inserted into the second rotary in the external sleeve 15a of the handle 15 and rigidly connected thereto by means of a circlip 25 and positioned circumferentially by a radial pin 26 secured to the front part 27.

A cavity 29 formed in the head of 27a is arranged to receive illuminating means in the form of an electrical miniature bulb 1 cemented or crimped in a conducting holder 1a screwed in the head 27a. This holder 1a has two diametral slots 1c formed therein so that the holder can be screwed in or out by means of a suitable screwdriver. The angle of inclination of the recess 29 relative to the tool axis is such that the light rays emitted by the bulb 1 are or a range of the tool directed towards the treatment area at the tool end. The ground terminal of bulb 1, that is, the external socket of the bulb base, is held in close contact, for example by welding, with the bulb holder 1a engaging in turn with the ground-forming body of the front part 27 also made of a suitable conducting metal. The other or input terminal of bulb 16, which is the central contact of the bulb base, engages with a front metal ring 2 crimped on a support 3 made of insulating material acting as a front bearing or supporting a bearing in which the first rotary shaft 28 is rotatably mounted. This front metal ring 2 is supplied with electric current through an insulated wire 4 having one end welded to the front ring 2 and its other end welded to another or rear metal ring 5 crimped in turn to another insulating support 6 acting as a rear bearing or supporting another bearing for the rotary shaft 28.

Since the front part 27 must be separated from the handle 15, the current is fed to this second ring 5 via a resilient contact composed of a spring blade 9 having one thereof embedded in an inner conducting socket 11 forming an integral part of handle 15. This spring blade 9 extends axially in the handle 15 and can be caused to engage with the rear metal ring 5 at will through a switch 7 of the push-knob or push-button type which is slidably fitted in a ring 8 embedded in turn in the external sleeve 15a of handle 15. The push-knob head is mushroom-shaped to prevent the ingress of dust and foreign substances into the contra-angle. When the push-knob 7 is depressed by one of the fingers of the user's hand holding the handpiece, the spring blade 9 is deflected and moved towards the rear ring 5, thus closing the contract. Therefore, the dental surgeon can turn on the bulb only when necessary, without necessarily actuating the tool at the same time. The circuit or electrical connecting means is opened automatically when the contra-angle is released because the push-knob 7 is restored automatically to its inoperative position by the spring blade 9 acting as a return spring. Thus, the operator has the certainty that when the contra-angle is not in use the bulb will remain deenergized.

The spring blade 9 is supplied with electric current by means of an insulated conducting wire 23 housed in a groove formed in another inner sleeve 14 composed of conducting metal. The front end of wire 23 is welded to the spring blade 9 and its rear end is in electrical contact with matching contact means in the form of an annular conducting track 21 surrounding concentrically the second shaft 28a and constituting the rear end of the handle.

The other electric line constituting ground-connecting means comprises the inner sleeves 11, 14 made of conducting metal which are fitted in the handle 15. The sleeve 11 is embedded in the inner sleeve 14 so as to be in sliding contact engagement therewith, and these sleeves 11 and 14 are assembled by means of a ring nut 16 locked against rotation or release by a pin 17. On the rear surface of handle 15 the ground line terminates with the matching contact means in the form of an annular track 18 composed of a metal ring surrounding concentrically the other annular track 21 and secured to the sleeve 14 so as to hold in position an insulating ring 20 separating the outer ring 18 from the inner track 21(FIGS. 1b and 2).

Mounted in the sleeve 11 are two bearings 12, 13 in which the shaft 28a is rotatably mounted. In addition, an orifice is formed in sleeve 11 in case the circulation of a cooling fluid is contemplated. In the example illustrated, this orifice is closed by a metal plug 11a. Preferably, the outer sleeve 15a is made of light alloy. To ensure an efficient contact between the conducting body of the front part 27 and the sleeve 11 of handle 15, a resilient contact 24 is provided, for example, in the form of a rod embedded at its rear end in sleeve 11 and curved at the front end so as to constantly engage with a bevelled portion of the body of front part 27. The rod 24 is deflected provide a good electrical contact. Thus, a simple yet efficient and reliable electrical connection is obtained between the two parts of the contra-angle while permitting the easy and quick assembly and disassembly thereof by firstly pulling the front part 27 out of handle 15, this movement causing the circlip 25 to yield inwards, and subsequently extracting from the handle 15 the complete assembly enclosed in the sleeve 14, by unscrewing the nut 16, Moreover, the same handle 15 can be used with different heads.

Figure 1B:
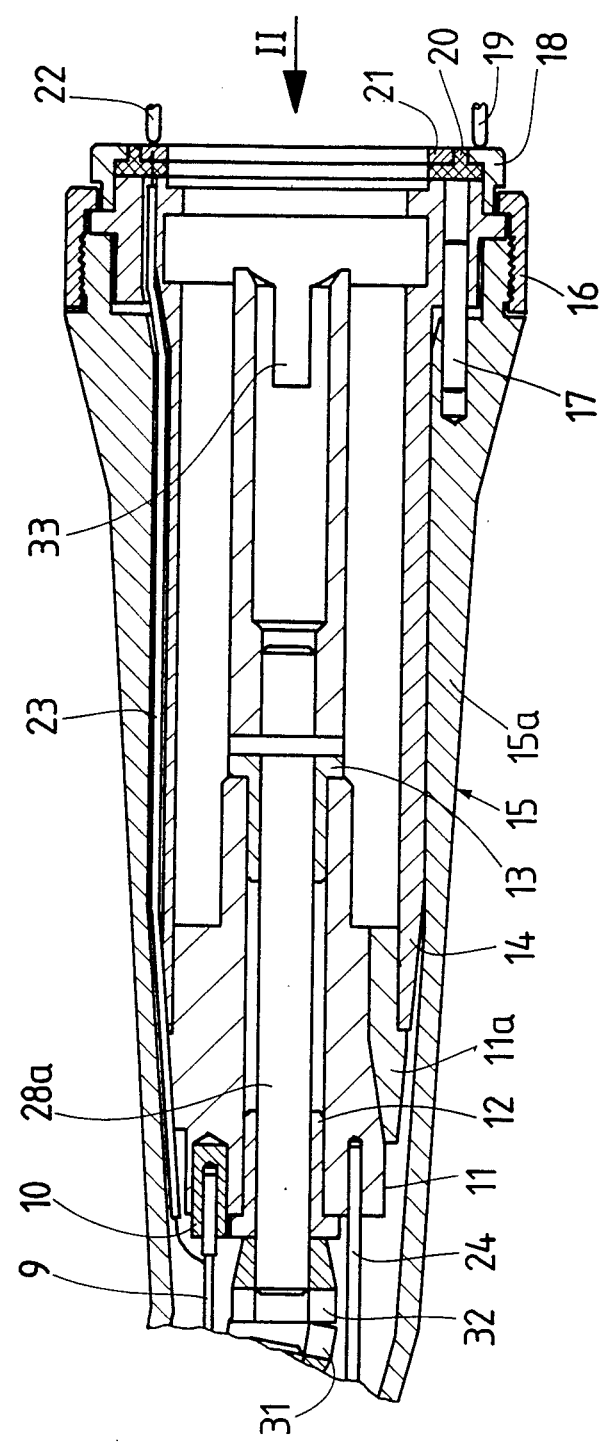
FIG. 1b is a similar view showing the rear section of the handpiece.
Figure 2:
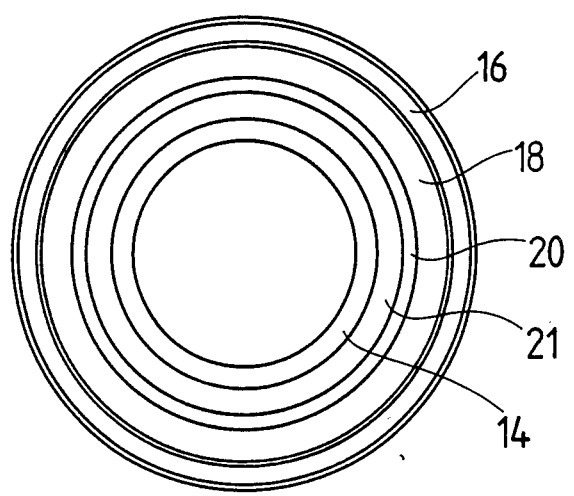
FIG. 2 is a view taken in the direction of the arrow II of FIG. 1b.

This handpiece is arranged to be driven by a suitable pneumatic or electric micromotor (not shown) housed in a rear socket arranged to be fastened to the rear end of handle 15 and comprising two contacts 19 and 22, respectively, consisting of spring-loaded pistons, as shown in FIG. 1b, and arranged to engage with the annular tracks 18, 21 of the matching contact means of the handle. The electric power for energizing the bulb 1 may be derived either from conductors leading from the power unit and incorporated in the cable supplying electric current to the electric or air motor, or from a rechargeable or non-rechargeable battery housed in said rear socket.

The handpiece may be arranged to be driven conventionally by an external motor via a belt and pulley transmission system, instead of by a micro-motor, and in this case the member carrying the electric contacts will comprises a connecting socket enclosing the motion converting means and the battery.

I claim:

1. A dental contra-angle handpiece having means for illuminating the treatment area comprising: a front part including a head having a tool holder therein for clamping a tool, and at least one miniature bulb disposed on the head and having a central contact; a handle detachably connected to said front part at a front end of the handle and provided with matching contact means on a rear end of the handle; a rotary shaft mounted in said front part for driving said tool; insulating support means disposed in said front part for rotatively supporting the rotary shaft; a rear socket fitted to the rear end of said handle and provided with electric contact means disposed to engage with the matching contact means for supplying electric power to said bulb; electrical connection means for electrically connecting the central contact of said bulb to the matching contact means comprising a front metal ring electrically connected to the central contact of the bulb, a rear metal ring electrically connected to the front metal ring, said front and rear metal rings being axially spaced from each other and mounted on the insulating support means , and a spring blade mounted in said handle and electrically connected to the matching contact means and extending axially at a junction between said front part and said handle, said spring blade being spaced from said rear metal ring when the front part and the handle are assembled with each other; and a switch mounted on said handle adjacent to said spring blade, said switch being operative to move said spring blade for engagement with said rear metal ring and thus close the electrical connection means.

2. The handpiece according to claim 1; wherein said matching contact means comprises a pair of concentric annular tracks.

3. The handpiece according to claim 1, including means for ground-connecting the bulb to the matching means, said means comprising conducting-metal component elements of said front part and said handle, and means for interconnecting electrically said front part and said handle in their assembled condition having a resilient contact element secured to, and extending axially in an end portion of one of the front part and handle and resting resiliently against one face of a conducting element of the other of the front part and handle.

4. The handpiece according to claim 1, wherein the means for ground-connecting said bulb includes a metal holder detachably screwed in the head for receiving the bulb.

5. The handpiece according to claim 4, wherein said metal holder is provided with a slot engageable with a screwdriver.

6. A dental contra-angle handpiece comprising: a head; a tool holder rotatively disposed in the head for receiving a tool therein during the use of the dental contra-angle handpiece; illuminating means disposed adjacent to the tool holder on the head for illuminating a working range of the tool, the illuminating means having an input terminal and an electrically grounded ground terminal; a tubular arm rearwardly extending from the head; a first rotary shaft rotatively disposed within the tubular arm, a front end of the first rotary shaft being connected to the tool holder to drive the same; bearing means composed of electrically insulating material and disposed between the inner surface of the tubular arm and the peripheral surface of the first rotary shaft for rotatively supporting the first rotary shaft; a tubular handle detachably engaged at its front end with the rear end of the arm; a second rotary shaft rotatively disposed within the tubular handle, the front end of the second rotary shaft being detachably engaged with the rear end of the first rotary shaft to rotate the same; matching means disposed at the rear end of the handle for receiving electric power from an external power supply source; connecting means for electrically connecting the input terminal of the illuminating means to the matching contact means so as to feed electric power to the illuminating means, the connecting means including a front metal ring electrically connected to the input terminal and disposed adjacent to the illuminating means around the bearing means, a rear metal ring electrically connected to the front metal ring and disposed at the rear end portion of the arm around the bearing means, and a blade disposed within the handle, the rear end of the blade being electrically connected to the matching contact means and the front end of the blade extending adjacent to the rear metal ring; and switch means disposed on the handle and manually operative to act on the front end of the blade so as to establish electrical contact between the front end of the blade and the rear metal ring.

7. A dental contra-angle handpiece according to claim 6; wherein the switch means comprises a push-button switch.

8. A dental contra-angle handpiece according to claim 7; wherein the front of the blade is disposed between the push-button switch and the rear metal ring.

9. A dental contra-angle handpiece according to claim 8; wherein the blade comprises a spring blade for normally urging the push-button switch away from the metal ring.

10. A dental contra-angle handpiece according to claim 6; including a wire electrically connected between the front and rear metal rings.

11. A dental contra-angle handpiece according to claim 6; wherein the illuminating means comprises a bulb.

12. A dental contra-angle handpiece according to claim 11; including an electrically conducting holder for holding the bulb therein.

13. A dental contra-angle handpiece according to claim 12; wherein the head means defining a cavity therein for detachably receiving the conducting holder.

14. A dental contra-angle handpiece according to claim 6; wherein the matching contact means comprises a first annular track for receiving electric power, a second annular track spaced from and concentric with the first annular track and being ground-connected, and an insulating ring disposed between the first and second annular tracks.

15. A dental contra-angle handpiece according to claim 14; including means for ground-connecting the ground terminal of the illuminating means to the second annular track.

16. A dental contra-angle handpiece according to claim 15; wherein the means for ground-connecting comprises a metal tubular arm eletrically connected to the ground terminal of the illuminating means, and a rod disposed within the handle, the rear end of the rod being electrically connected to the matching contact means and the front end of the rod being in resilient and electrical contact with the rear end of the tubular arm.

17. A dental contra-angle handpiece according to claim 6; including means detachably connecting the rear end of the tubular arm and the front end of the tubular handle.

18. A dental contra-angle handpiece according to claim 17; wherein the means detachably connecting includes a clip disposed between the arm and handle.

19. A dental contra-angle handpiece according to claim 6; including a rear socket detachably connected to the matching contact means for feeding electrical power to the matching contact means.

* * * * *